United States Patent
Trieu et al.

(10) Patent No.: US 8,011,250 B2
(45) Date of Patent: Sep. 6, 2011

(54) APPARATUS AND METHOD FOR CONTROLLING AND MONITORING THE PRESSURE IN PRESSURE LINE OR PIPES

(75) Inventors: Hoc Khiem Trieu, Kamp-Lintfort (DE); Peter Wiebe, Duisburg (DE); Robert Klieber, Dortmund (DE)

(73) Assignee: Fraunhofer-Gesellschaft zur Foerderung der angewandten Forschung e.v., Munich (DE)

( * ) Notice: Subject to any disclaimer, the term of this patent is extended or adjusted under 35 U.S.C. 154(b) by 79 days.

(21) Appl. No.: 12/520,314

(22) PCT Filed: Dec. 22, 2006

(86) PCT No.: PCT/EP2006/012513
§ 371 (c)(1),
(2), (4) Date: Jul. 29, 2009

(87) PCT Pub. No.: WO2008/083692
PCT Pub. Date: Jul. 17, 2008

(65) Prior Publication Data
US 2010/0089167 A1   Apr. 15, 2010

(51) Int. Cl.
*A61B 6/00* (2006.01)
*G01L 7/00* (2006.01)
(52) U.S. Cl. ............... 73/700; 600/432; 600/431
(58) Field of Classification Search ............ None
See application file for complete search history.

(56) References Cited

U.S. PATENT DOCUMENTS

| | | | |
|---|---|---|---|
| 5,808,203 A | | 9/1998 | Nolan, Jr. et al. |
| 5,882,343 A | * | 3/1999 | Wilson et al. .......... 604/246 |
| 5,993,412 A | * | 11/1999 | Deily et al. .......... 604/68 |
| 6,656,157 B1 | * | 12/2003 | Duchon et al. .......... 604/131 |
| 2002/0022807 A1 | * | 2/2002 | Duchon et al. .......... 604/228 |
| 2005/0015056 A1 | * | 1/2005 | Duchon et al. .......... 604/218 |
| 2005/0267363 A1 | * | 12/2005 | Duchon et al. .......... 600/432 |
| 2009/0149743 A1 | * | 6/2009 | Barron et al. .......... 600/431 |
| 2009/0221914 A1 | * | 9/2009 | Barrett et al. .......... 600/431 |
| 2010/0249587 A1 | * | 9/2010 | Duchon et al. .......... 600/432 |

FOREIGN PATENT DOCUMENTS

| WO | 00/72900 A1 | 12/2000 |
|---|---|---|
| WO | 01/72357 A2 | 10/2001 |
| WO | 2005/102416 A1 | 11/2005 |
| WO | 2006/116997 A1 | 11/2006 |

OTHER PUBLICATIONS

Official Communication issued in International Patent Application No. PCT/EP2006/012513, mailed on Sep. 4, 2007.

* cited by examiner

*Primary Examiner* — Andre J Allen
(74) *Attorney, Agent, or Firm* — Keating & Bennett, LLP

(57) ABSTRACT

An apparatus including a chamber having a chamber opening, a plunger which is movable within the chamber so as to change a chamber volume, which is defined by the plunger and a chamber wall and which adjoins the chamber opening, includes a measurer for measuring a pressure within the chamber or for measuring a force F, F being the force which acts upon the plunger so as to change the chamber volume.

10 Claims, 2 Drawing Sheets

APPARATUS AND METHOD FOR CONTROLLING AND MONITORING THE PRESSURE IN PRESSURE LINE OR PIPES

The present invention relates to an apparatus and a method suited, in particular, to measure, monitor and control pressure in pressure lines or pipes.

BACKGROUND OF THE INVENTION

In biological or medical applications, use is often made of syringes to introduce e.g. liquids into (pressure) lines or pipes. When using a syringe, a more or less large amount of force may be used for introducing an exemplary liquid or gas, depending on the pressure present in the pressure lines or pipes. Normally, the pressure in said lines is measured in that a sensor for measuring the pressure, i.e. a pressure sensor, is mounted directly on the pipings. However, this approach may turn out to be difficult, since it is useful, for this purpose, to integrate the sensor into the piping or, if this is not possible, to find a complicated setup for connecting the sensor to the line, or to the interior thereof. This would be possible if the line is elastic and if pressure measurement of the internal pressure of the line may be effected, for example, by means of measuring the voltage of the elastic line, e.g. by measuring a force that may be used for deforming the elastic line (e.g. for squeezing the line.

However, if the line is not elastic, as is the case, for example, with a line having a very thin diameter, it will be difficult to perform this measurement technique. If this is not possible or not accurate enough, the line would have to comprise a hole so as to be able to thereby measure the internal pressure directly. In turn, this may result in a pressure drop or a leak.

SUMMARY

According to an embodiment, an apparatus may have: a chamber having at least one chamber opening; a plunger which is movable within the chamber so as to change a chamber volume which is defined by the plunger and a chamber wall, and which adjoins the chamber opening; and a measurer for measuring a pressure within the chamber or for measuring a force F which acts upon the plunger so as to change the chamber volume.

According to another embodiment, a method may have the steps of: providing a chamber having at least one chamber opening, a plunger which is movable within the chamber and defines a chamber volume, the chamber volume adjoining the chamber opening and being defined by the plunger and a chamber wall; and measuring a pressure within the chamber; or measuring a force acting upon the plunger.

The present invention is based on the finding that the pressure of a measurement medium within a line may be measured in that the measurement medium is connected to a chamber via a chamber opening and that the chamber further comprises a movable plunger, a movement of the plunger resulting in a change in a chamber volume. Following equalization of pressure between a medium within the chamber and the measurement medium within the line, the pressure of the measurement medium within the line may be measured by performing pressure measurement within the chamber. Alternatively, a force acting upon the plunger may be measured. The chamber comprising the plunger may be a syringe, for example, in which case the syringe, in accordance with the invention, either comprises a means for measuring the pressure or for measuring the force, or is connected, via an optional adapter, to a means for measuring a force or a pressure.

This is advantageous in particular when it is in any case useful, irrespective of the pressure measurement, to utilize a syringe, for example to introduce a liquid into the line. In such a case, one may simultaneously measure the force which is to be exerted onto the syringe once the needle of the syringe has been introduced into the line, so as to withstand the pressure within the line, for example, or to determine the force that may be used for introducing, e.g., a certain volume of the medium into the line within a certain amount of time. Thus, the syringe may be utilized both as injection equipment and as an apparatus for measuring the force and/or pressure.

However, the inventive concept is not limited to lines comprising liquids and to measuring the pressure thereof, but may similarly be applied to lines containing gaseous substances.

In accordance with the invention, the pressure within the line, or within a pipe, or within the syringe itself is therefore measured even in that force measurement is conducted, the force measured corresponding to the force to be exerted on a plunger of the syringe, so that the medium within the syringe will enter into the line. On the other hand, the pressure may be determined directly by means of a pressure sensor which is direct contact with the content of the syringe. Since the pressure is a measure of the force acting on a unit of area, the pressure, e.g. within the line, may be calculated by measuring the force and the surface area A (the cross-sectional area). If, for example, the syringe has a circular cross-section with a radius r, the pressure P may be calculated using the force F acting upon the plunger of the syringe, by means of $P=F/A$, wherein $A=\pi r^2$. The force F in this formula is the force that may be used for keeping the plunger in a fixed position once pressure equalization between the chamber of the syringe and the internal pressure of the line has been performed.

Thus, the present invention comprises the following important aspects: pressure measurement within a pressure line or a pipe or a syringe is performed, by means of a sensor, with regard to the force or the pressure which acts upon the syringe, for example, the syringe being connected to the line or the pipe.

The exemplary pressure sensor may be integrated into the housing of the syringe, for example, and may possibly comprise a pressure transducer medium which, if useful, comprises a membrane for separating the pressure transducer medium or the pressure sensor from the surroundings. On the other hand, the pressure sensor may also be accommodated within a housing which is connected to the plunger of the syringe and generates a pressure within the pressure sensor by pressing the syringe. In this manner, the pressure within the syringe and/or the pressure within the line or the pipe may be determined by measuring the pressure within the pressure sensor. A pressure transducer medium is liquid or gaseous, for example, and transduces a force acting upon the plunger, for example, to a pressure of the pressure transducer medium, or forwards this pressure to the sensor. Advantageously, it should not be highly compressible so as to enable immediate forwarding.

On the other hand, a force sensor may be used for directly measuring the force exerted on the syringe to be able to withstand the pressure within the line, or the force which may be used as a minimum for introducing the medium within the syringe into the line. Thus, the pressure within the syringe and, as a result, eventually the pressure within the line may be calculated as was described above while using the cross-sectional area A of the syringe, or the surface area of the plunger of the syringe.

Additionally, it is also possible to combine both aspects into a modular setup while using an adapter. In this context, the adapter is implemented to establish a connection between the selected syringe and the pressure, or force, sensor. Advantageously, the adapter is implemented such that it fits onto a conventional syringe or onto a plunger of a conventional syringe, and that, on the other hand, it may be coupled to the pressure, or force, sensor. While using various adapters, which are adapted to the plungers of the various syringes, any conventional syringe may eventually be employed for pressure measurement in combination with the (universal) pressure, or force, sensor.

Other features, elements, steps, characteristics and advantages of the present invention will become more apparent from the following detailed description of preferred embodiments of the present invention with reference to the attached drawings.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
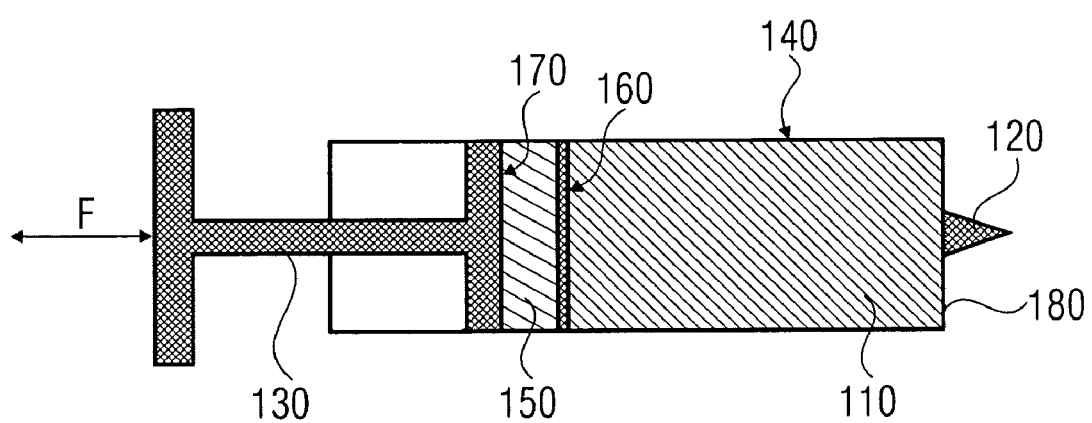
FIG. 1 shows an apparatus comprising a variable chamber and a means for measuring the pressure.

Before the present invention will be explained in more detail below with reference to the figures, it shall be noted that elements in the figures which are identical or have identical actions are designated by identical or similar reference numerals, and that repeated descriptions of said elements have been omitted.

FIG. 1 shows an apparatus comprising a chamber 110 having a chamber opening 120 and a plunger 130, the plunger 130 being formed by a chamber volume which is bounded by a chamber wall 140, the plunger 130, on the one hand, and a floor 180 comprising the chamber opening 120, on the other hand. In addition, the apparatus comprises a means 150 for measuring a pressure within the chamber 110 or for measuring a force acting upon the plunger 130 so as to change the chamber volume.

In this context, the means 150 comprises a sensor area 160, which in the embodiment selected here is identical with a cross-sectional area 170 perpendicular to the direction of motion of the plunger 130. In other embodiments, the sensor area 160 extends only across some of the cross-sectional area 170. The pressure P may be determined as follows using the surface area A of the sensor area 160 and the force F acting upon the plunger 130 so as to change the volume of the chamber 110: $P=F/A$. A tractive force (e.g. a negative sign of the force F) corresponds to a negative pressure within the line, while overpressure corresponds, e.g., to a positive sign of the force F.

In further embodiments, the means 150 is arranged at different positions. For example, the means 150 may be arranged along a side portion of the wall 140, or it may be arranged, provided that it has a corresponding opening, on the floor 180 with the opening 120. Also, the means 150 may comprise either a display indicating the pressure or the force acting upon it, or the means 150 is connected to an electronic evaluation system in a wireless manner or via lines, said electronic evaluation system not being shown in the present drawing.

In a further embodiment, the pressure within the chamber 110 may be determined in that a constant force acts upon the plunger 130 and in that a time is measured during which a specific volume is introduced into the line through the chamber opening 120 (not shown in the figure).

Figure 2:
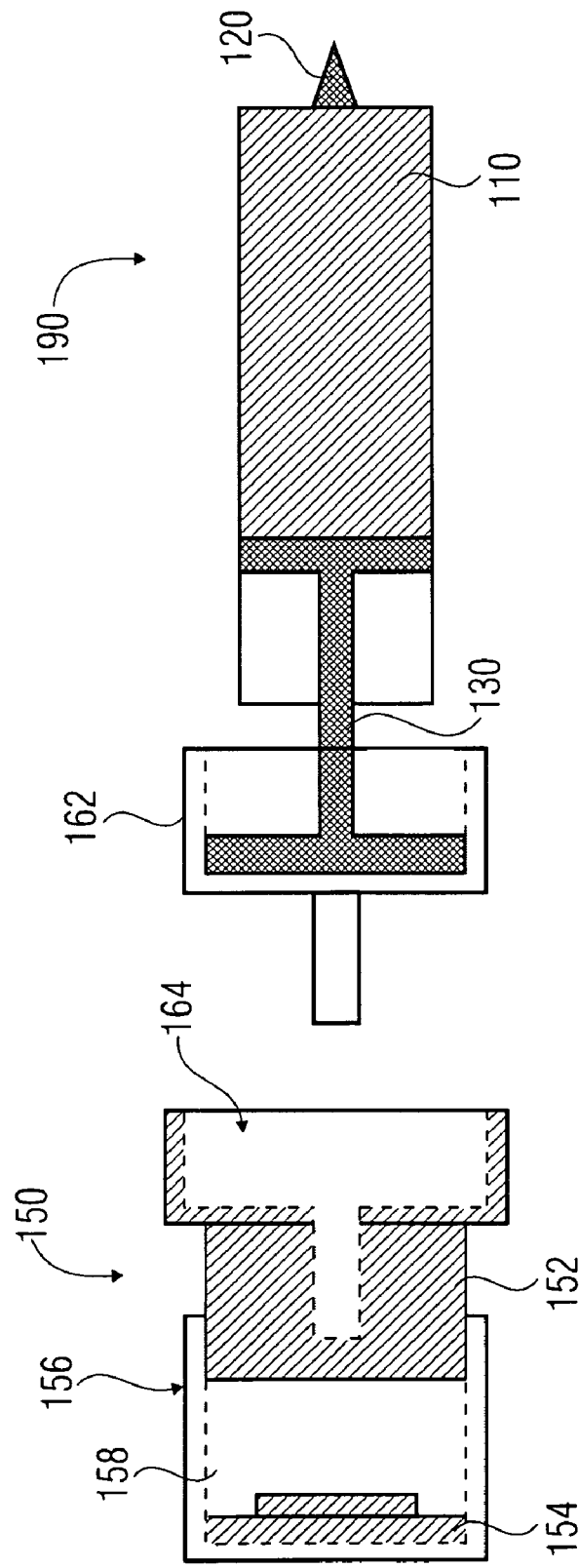
FIG. 2 shows a pressure sensor connected to a syringe via an adapter.

FIG. 2 shows a means 150 for measuring the pressure, or the force, which is connected to an adapter for a syringe 190. The syringe 190 comprises the chamber 110 having the chamber opening 120 and the plunger 130, said plunger in turn being movable and changing the volume of the chamber 110 by said movement. In this embodiment, a pressure sensor is used for measuring a force that may be used for pressing the syringe 190. The means 150 comprises a stamp 152 and a sensor 154 arranged on a housing 156 with a pressure transducer medium 158. This modular arrangement further comprises an adapter 162, which is implemented such that the plunger 130, on the one hand, and the adapter 162, on the other hand, fit an opening 164 of the means 150. Advantageously, the adapter 162 is adapted for a given syringe 190; i.e. while using various adapters which differ with regard to their openings for the plungers 130, the means 150 may be employed for various syringes 190. Thus, a simple connection may be established for each available syringe 190 to the means 150 for measuring the pressure or for measuring the force. Therefore, the means 150 is universally usable.

It is an advantage of the present invention that it is possible, by using the adapters 162 and 150, not only to measure or to calculate the pressure within lines or pipes or syringes in a controlled manner, but to avoid the line being overloaded due to excessive pressure. Exceeding a critical threshold value may be indicated, for example, by an optical or an acoustic signal. Alternatively, an electrical signal may also be sent to an electronic evaluation system (not shown). Pressure measurement within the sensor 154 may be performed, for example, by means of various piezo or thin-film sensors or by means of resistance measurement within a ceramic measuring cell.

In summary, the present invention therefore offers a simple and low-cost possibility of determining the pressure within lines while using conventional syringes 190. In addition, the present invention may be used as a protection by means of which too high a load of the line caused by generation of excessive pressure within the line, for example while a medium is being injected, is avoided.

The present invention is therefore advantageous in particular when a syringe 190 is used anyhow for a present application, for example for introducing or extracting a liquid or gas into or from a line or pipe. In this case, the syringes 190 used may be employed for measuring the pressure while using the stamp 152 or the adapter 162. In accordance with the invention, it is therefore possible to measure both the pressure which is larger as compared to the ambient pressure, and a negative pressure within the lines. In this context, a negative pressure makes itself felt in that the force acting upon the plunger 130 or the force F which may be used for fixing the plunger 130 in a given position, acts as a tractive force in the direction of the chamber opening 120. On the other hand, a compressive force F which acts on the plunger 130 is a force which is directed away from the chamber opening 120.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A modular arrangement comprising:
   a syringe comprising:
      a chamber comprising at least one chamber opening; and
      a plunger which is movable within the chamber along a plunger axis so as to change a chamber volume which is defined by the plunger and a chamber wall, and which adjoins the chamber opening;
   a measurer configured to measure a force which acts upon the plunger so as to change the chamber volume; wherein
   the measurer comprises a stamp and a housing with the stamp being movable within the housing along a stamp axis so that a pressure within a pressure vessel defined by the housing and the stamp changes due to movement of the stamp, the measurer further comprising a sensor arranged within the pressure vessel, the sensor being configured to measure a pressure within the pressure vessel; and
   an adapter arranged to be fit to an end of the plunger facing away from the chamber volume and to be fit to an end of the stamp facing away from the pressure vessel so that the measurer is connectable with the syringe such that the stamp axis and the plunger axis are parallel or substantially parallel to each other and the pressure within the pressure vessel changes in accordance with a pressure within the chamber volume.

2. The modular arrangement as claimed in claim 1, wherein a pressure transducer medium is arranged within the pressure vessel.

3. The modular arrangement as claimed in claim 1, wherein the measurer configured to measure the force is adapted to measure the force which acts upon the plunger in the direction of the at least one chamber opening.

4. The modular arrangement as claimed in claim 1, wherein the at least one chamber opening comprises a drain tube.

5. The modular arrangement as claimed in claim 1, wherein the at least one chamber comprises pressure transducer medium.

6. The modular arrangement as claimed in claim 1, wherein the measurer is arranged to emit a warning signal, including at least one of an optical, acoustic or electrical signal, when a value of the pressure within the chamber volume reaches an upper threshold value.

7. The modular arrangement as claimed in claim 5, wherein the pressure transducer medium is separated from a surrounding exterior thereof by a membrane.

8. A method comprising:
   providing a syringe comprising:
      a chamber comprising at least one chamber opening; and
      a plunger which is movable within the chamber along a plunger axis so as to change a chamber volume which is defined by the plunger and a chamber wall, and which adjoins the at least one chamber opening;
   providing a measurer arranged to measure a force which acts upon the plunger so as to change the chamber volume, wherein the measurer comprises a stamp and a housing with the stamp being movable within the housing along a stamp axis so that a pressure within a pressure vessel defined by the housing and the stamp changes due to movement of the stamp;
   fitting an adapter to an end of the plunger facing away from the chamber volume and to an end of the stamp facing away from the pressure vessel so that the measurer is connected with the syringe such that the stamp axis and the plunger axis are parallel or substantially parallel to each other and the pressure within the pressure vessel changes in accordance with a pressure within the chamber volume; and
   measuring a pressure within the pressure vessel.

9. The method as claimed in claim 8, wherein measuring the pressure comprises signaling that a maximum pressure has been reached.

10. A modular arrangement comprising:
    a measurer arranged to measure a force which acts upon a plunger of a syringe, the measurer comprising a stamp and a housing with the stamp being movable within the housing along a stamp axis so that a pressure within a pressure vessel defined by the housing and the stamp changes due to movement of the stamp, the measurer further comprising a sensor arranged within the pressure vessel, the sensor being arranged to measure a pressure within the pressure vessel; and
    an adapter arranged to be fit to an end of the plunger of the syringe facing away from a chamber volume defined by the plunger and a chamber wall of a chamber of the syringe within which the plunger is movable along a plunger axis, and to be fit to an end of the stamp facing away from the pressure vessel so that the measurer is connectable with the syringe such that the stamp axis and the plunger axis of the syringe are parallel or substantially parallel to each other and the pressure within the pressure vessel changes in accordance with a pressure within the chamber volume.

* * * * *